United States Patent
Krause-Kyora et al.

(10) Patent No.: US 12,295,924 B2
(45) Date of Patent: May 13, 2025

(54) STABLE WOUND HEALING OINTMENT

(71) Applicant: BEIERSDORF AG, Hamburg (DE)

(72) Inventors: Felix Krause-Kyora, Hamburg (DE); Susanne Scheidweiler, Buxtehude (DE); Alexander Filbry, Hamburg (DE); Daniel Richter, Norderstedt (DE)

(73) Assignee: BEIERSDORF AG, Hamburg (DE)

( * ) Notice: Subject to any disclaimer, the term of this patent is extended or adjusted under 35 U.S.C. 154(b) by 1264 days.

(21) Appl. No.: 16/966,194

(22) PCT Filed: Jan. 29, 2019

(86) PCT No.: PCT/EP2019/052065
§ 371 (c)(1),
(2) Date: Jul. 30, 2020

(87) PCT Pub. No.: WO2019/149677
PCT Pub. Date: Aug. 8, 2019

(65) Prior Publication Data
US 2021/0038542 A1 Feb. 11, 2021

(30) Foreign Application Priority Data
Feb. 2, 2018 (DE) .................. 102018201598.8

(51) Int. Cl.

| | | |
|---|---|---|
| *A61K 31/16* | (2006.01) | |
| *A61K 8/34* | (2006.01) | |
| *A61K 8/37* | (2006.01) | |
| *A61K 8/42* | (2006.01) | |
| *A61K 8/92* | (2006.01) | |
| *A61K 31/047* | (2006.01) | |
| *A61K 47/10* | (2017.01) | |
| *A61K 47/14* | (2017.01) | |
| *A61K 47/44* | (2017.01) | |
| *A61Q 19/00* | (2006.01) | |

(52) U.S. Cl.
CPC .............. *A61K 31/16* (2013.01); *A61K 8/342* (2013.01); *A61K 8/345* (2013.01); *A61K 8/37* (2013.01); *A61K 8/42* (2013.01); *A61K 8/92* (2013.01); *A61K 31/047* (2013.01); *A61K 47/10* (2013.01); *A61K 47/14* (2013.01); *A61K 47/44* (2013.01); *A61Q 19/007* (2013.01)

(58) Field of Classification Search
CPC ........ A61K 31/16; A61K 8/342; A61K 8/345; A61K 8/37; A61K 8/42; A61K 8/92; A61K 31/047; A61K 47/10; A61K 47/14; A61K 47/44; A61K 2800/30; A61K 2800/31; A61K 8/31; A61K 8/375; A61Q 19/007; A61Q 19/00
See application file for complete search history.

(56) References Cited

U.S. PATENT DOCUMENTS

| | | | |
|---|---|---|---|
| 4,436,738 A | 3/1984 | Bequette et al. | |
| 4,868,220 A | 9/1989 | Scheuffgen | |
| 5,688,949 A | 11/1997 | Inoue et al. | |
| 2002/0128615 A1 | 9/2002 | Tyrrell et al. | |
| 2003/0103916 A1 | 6/2003 | Imanaka et al. | |
| 2004/0258717 A1* | 12/2004 | Sauermann | A61Q 19/007 424/400 |
| 2005/0053570 A1 | 3/2005 | Hirai et al. | |
| 2007/0110704 A1 | 5/2007 | Gallinat et al. | |
| 2012/0009234 A1 | 1/2012 | Origuchi et al. | |
| 2015/0034116 A1 | 2/2015 | Salese et al. | |
| 2016/0015752 A1* | 1/2016 | Lait | A61P 17/00 424/59 |
| 2016/0038451 A1 | 2/2016 | Makra | |
| 2016/0346173 A1* | 12/2016 | Scherer | A61K 8/345 |

FOREIGN PATENT DOCUMENTS

| | | |
|---|---|---|
| DE | 102015209752 A1 | 12/2016 |
| EP | 0093341 A2 | 11/1983 |
| EP | 0591528 A1 | 4/1994 |
| EP | 0992236 A1 | 4/2004 |
| EP | 1449510 A1 | 8/2004 |
| EP | 2380557 A1 | 10/2011 |
| JP | H07233088 A | 9/1995 |
| JP | H10259136 A | 9/1998 |
| KR | 20160056437 A | 5/2016 |
| WO | 02060502 A2 | 8/2002 |
| WO | 2005053680 A1 | 6/2005 |
| WO | 2013082430 A1 | 6/2013 |

OTHER PUBLICATIONS

Endimulse 165V. (2012). https://www.coastsouthwest.com/app/webroot/files/uploads/Endimulse_165V_TDS.pdf . (Year: 2012).*

* cited by examiner

*Primary Examiner* — David J Blanchard
*Assistant Examiner* — Janet Joseph
(74) *Attorney, Agent, or Firm* — Abel Schillinger, LLP

(57) ABSTRACT

Described is a stable cosmetic or dermatological formulation, in particular a wound healing ointment, which comprises a.) 0.8 to 3 wt.-%, in particular 1.2 to 1.8 wt.-% glyceryl stearates, b.) 0.8 to 3 wt.-%, in particular 1.2 to 1.8 wt.-% glyceryl stearates SE, c.) one or more lipids selected from the group of ceresin, cera microcristallina and paraffinum liquidum, advantageously 8 to 12 wt.-%, in particular 9 to 11 wt.-% ceresin, d.) less than 1 wt.-% water, and e.) less than 0.1 wt.-% of each of cholesterol and lanolin alcohol.

20 Claims, No Drawings

STABLE WOUND HEALING OINTMENT

BACKGROUND OF THE INVENTION

1. Field of the Invention

The invention is a cosmetic or dermatological formulation, in particular a wound healing ointment, comprising two specific emulsifiers in specific proportions and one or more lipids selected from the group of ceresin, cera microcristallina and paraffinum liquidum, preferably as far as possible without constituents of animal origin.

2. Discussion of Background Information

Ointments, pastes and hydrogels, such as Bepanthen© wound healing ointment, Aquaphor® or Fenistil®, are known from the field of wound healing.

Consumers are increasingly demanding that substances of animal origin be avoided in cosmetics.

However, the stability criteria in particular should continue to be met.

The problem underlying the present invention was therefore to provide a stable ointment formulation.

Problems with ointment bases of the prior art are:
the appearance changes over time
often yellow-orange-brownish coloration, shiny, somewhat translucent
loss of stability:
consistency increase over the lifetime
at elevated temperatures, e.g. 40° C., significant oiling out occurs
at elevated temperatures (40° C.) and under the influence of light, there is a distinct discoloration towards dark orange-brown
the odor deteriorates significantly at elevated temperatures and under the influence of light
These disadvantages should be avoided or reduced.

SUMMARY OF THE INVENTION

The problems are solved by a cosmetic or dermatological preparation comprising
a.) 0.8 to 3% by weight, particularly 1.2 to 1.8% by weight glyceryl stearate,
b.) 0.8 to 3% by weight, particularly 1.2 to 1.8% by weight glyceryl stearate SE,
c.) one or more lipids selected from the group of ceresin, cera microcristallina and paraffinum liquidum
d.) less than 1% by weight water and
e.) less than 0.1% by weight each of cholesterol and lanolin alcohol.

The proportions by weight are in each case based on the total weight of the preparation.

The preparation according to the invention advantageously comprises 8 to 15% by weight, particularly 9 to 12% by weight ceresin, based on the total mass of the preparation.

An advantage of the preparation according to the invention is that there is great regulatory freedom in terms of formulation, since on the one hand no constituents of animal origin are to be used, but on the other hand other additives can be added without causing stability problems.

The approach of not using any constituents of animal origin is that of excluding dead animal tissue or derived products.

In the absence of constituents of animal origin, lanolin alcohol and cholesterol in particular should be omitted.

Lanolin alcohols consist of the highly refined, unsaponifiable portion of wool wax which has subsequently been subjected to a molecular distillation in order to improve color and odor. Lanolin alcohols are a highly complex mixture of alcohols having an average molecular weight of ca. 370 Da, consisting of cholesterol, lanosterol, agnosterol and dihydro derivatives thereof and straight-chain and branched chain aliphatic alcohols. In addition to caring properties, they have excellent W/O emulsifier capability which is why they have been used in many cosmetics.

In cosmetic preparations, purified wool wax is used as co-emulsifier, highly adhesive lipid and superfatting agent. As an alternative to petroleum jelly, lanolin can be used as a nasal ointment to care for the mucous membranes.

Wool wax (also referred to as lanolin, wool fat, lat. Adeps lanae) is the secretion of the sebum glands of sheep which is obtained by washing sheep's wool.

Cholesterol is one of the non-ionogenic emulsifiers and is used primarily as emulsifier and stabilizer for emulsions of oil and water in various fields.

The cosmetics industry uses the substance for some cosmetics in their function as smoothing, emulsifying, skin caring, stabilizing and viscosity regulating ingredient for ointments and creams.

In addition, the chemical is used for the synthesis of derived compounds, particularly of cholesteryl esters, which are also processed in cosmetic products.

However, commercially traded and used cholesterol still originates from natural sources. To produce the pure chemical, the spinal cord of cattle and the wool fat (lanolin) of sheep are primarily used. It is usually produced by extraction with petroleum ether. The extracted material is then purified by repeated bromination.

In accordance with the invention, the addition of these substances of animal origin is avoided.

The proportion of cholesterol and lanolin alcohol is therefore in each case less than 0.1% by weight, especially 0% by weight, based on the total mass of the preparation. I.e. the proportion of at most 0.1% of these substances is ensured if lanolin alcohols or cholesterol have been introduced by impurities.

The formulation according to the invention is ideally anhydrous. However, since water may be introduced due to impurities, by means of additives such as glycerol, in the manufacturing process or during storage, the proportion of water should be less than 1% by weight, in particular less than 0.1% by weight, based on the total mass of the formulation, in order to be considered "anhydrous". A preparation according to the invention is considered to be anhydrous if the water content thereof is less than 1% by weight, particularly less than 0.1% by weight, based on the total mass of the preparation.

In accordance with the invention, the cosmetic or dermatological preparations comprise glyceryl stearate and glyceryl stearate SE.

Studies have shown that this combination, surprisingly, ensures the required stability.

Glyceryl stearate SE (CAS 11099-07-3) and glyceryl stearate (CAS 31566-31-1) are esters of stearic acid and glycerin.

Glyceryl stearate SE is a self-emulsifying variant of glyceryl stearate and comprises sodium and potassium stearates.

Glycerin stearate SE is a combination of mono- and diglycerides of vegetable oils and ca. 3 percent potassium stearate. The addition »SE« describes the self-emulsifying form of glycerin stearate which is achieved by potassium stearate (potassium soap).

In accordance with the invention, the proportion of glyceryl stearate and glyceryl stearate SE selected is in each case in the range from 0.8 to 3% by weight, particularly 1.2 to 1.8% by weight, based on the total mass of the preparation.

The lipid ceresin (CAS 8001-75-0) also called ceresin, cerosin, cerin, earth wax, mineral wax, ozocerotin or artificial wax) is produced by heating, with addition of 6 to 10% sulfuric acid, of ozocerite—an organic mineral that is obtained by mining and largely consists of hydrocarbons.

The preferred formulations according to the invention comprise highly viscous preparations containing lipid.

Highly viscous liquids, such as honey or syrup, have dynamic viscosities at 25° C. of more than 10 000 mPa*s.

The lipid-containing preparation preferably has a dynamic viscosity of more than 10 000 mPa*s at 25° C. and a shear rate of 10 $s^{-1}$. In particular, the lipid-containing preparation has a dynamic viscosity in the range from 15 000 to 30 000 mPa*s, especially in the range from 18 000 to 25 000 mPa*s at 25° C. and a shear rate of 10 $s^{-1}$ (measuring instrument Brookfield rotational viscometer; disc spindle 2).

Viscosity refers to the measure of the internal friction of liquid substances, a measure of the viscosity of a fluid. The reciprocal of viscosity is fluidity, a measure of the fluidity of a fluid. The greater (or higher) the viscosity, the more viscous, i.e. the less free-flowing the fluid is, the lower the viscosity, the thinner it is and the higher the fluidity.

A distinction is made between dynamic and kinematic viscosity. The dynamic viscosity is given in Pa s (Pascal second) and is usually determined with the aid of a rotational viscometer. The kinematic viscosity is measured in $m^2/s$. It indicates the internal friction of a liquid and is calculated by dividing the dynamic viscosity by the density of a liquid.

The consistency is in turn the resistance of a substance to its deformation.

The preparation according to the invention is advantageously formulated as an ointment. An ointment (lat. unguentum) or cream is understood according to the invention to be a semi-solid and advantageously homogeneous-looking preparation which is intended for use on the skin (e.g. as ointment) or on the mucous membranes. Ointments are used for local application of active ingredients or for care and protection of the skin, wounds or mucous membranes.

It consists primarily of an oily base made of natural or synthetic substances and can be a single-phase (e.g. ceresin, cera microcristallina and/or paraffinum liquidum) or multiphase system. Active ingredients or medicaments in solution or dispersion can be incorporated in the ointment or cream. The release of active ingredients from the ointment is possible and preferred according to the invention.

In the context of the invention, the term ointment includes
ointments in the narrower sense, single phase,
creams,
gels, lotions and
pastes An ointment according to the invention, which is particularly preferably anhydrous, comprises in particular all three preferred lipids, ceresin, cera microcrystallina and paraffinum liquidum.

Active ingredients may be present in the ointment or cream. Active ingredients are, in particular, natural additives.

Likewise, a particularly preferred application is the use of at least one active ingredient selected from anti-inflammatory or wound healing promoting active ingredients for local pain relief and anti-inflammation.

In addition, the use of at least one active ingredient selected from the group of antiseptics, antibiotics or antifungal agents for local wound disinfection and/or reduction in germ infestation has also proven to be advantageous.

The preparation may advantageously contain anti-inflammatory, wound-healing stimulating, pain-relieving or antimicrobial active ingredients.

For example, the preparation may contain anti-inflammatory or wound healing promoting active ingredients such as zinc acetate $2H_2O$, zinc sulfate $7H_2O$, allantoin, aloe vera, *Arnica*, bisabolol, *Calendula*, Chamomilae, dexpanthenol, enzyme inhibitors, Hamamelis, urea, honey/manuka honey, hyaluronic acid, St. John's wort, camomile extract, polidocanol, propolis, vitamins or provitamins, growth factors, e.g. PDGF, wheat germ extract, zinc oxide, vitamin A, vitamin C, vitamin E, chitosan, *Capsicum annuum* L. and derivatives, benzydamine, benzyl nicotinate, bufexamac, diclofenac, etofenamate, flufenamic acid, heparinoids, ibuprofen, indometacin, ketoprofen, naxoprophen, piroxicam, salicyclic acid and derivatives thereof, teniposide, 2-hydroxybenzoic acid, acetylsalicylic acid and derivatives, acidum silicicum D8, aconitum (monkshood), aconitum D3, aescin (horse chestnut), D4 ("dog parsley"), ammonium bituminosulfonate (ICHTHYOL®), *Arnica* D3, *Arnica* mont. D4, *Arnica montana* ex herba rec. ad usum ext, extract from guaiac wood, extract from *Arnica montana*, *Balsamum peruvianum* (Peru balsam), comfrey root fluid extract, benzyl nicotinate, *Calendula* ad usum ext., *Calendula* D3, *Calendula* Ø, *Calendula* offic. D3, *Calendula officinalis* Ø, camphor, *Chamomilla*, *Colchicum* e seminibus D4, *Conium* D2, Cort. Heisteriae, Cort. Salicis, D-camphor, Delphinium staph (larkspur), Delphinium staph. D4, dexpanthenol, diclofenac diethylamine, diclofenac sodium, diethylazane salt, dimethyl sulfoxide, *Echinacea* ang., *Echinacea* Ø, *Echinacea* purp., *Echinacea* purp. Ø, *Echinacea purpurea*, Planta tota Ø, Goldenrod herb, etofenamate extr., Flor Calendulae spiss, Extr. Fol digitalis fluid, Extr. Fol Hyoscyami fluid, Extr. Herba Conii maculate, Extr. Rad. Petasite. Spiss, Extr. Rhiz. Podophylli fluid., Extr. Semen Colchici fluid, Ferrum phosphoricum D10, spruce needle oil, flufenamic acid, fol. Betulae, Guaiacum Ø(guaiac resin), guaiac wood dry extract, witch hazel D4 ("witch hazel"), *Harpagophytum procumbens, Helianthus* ann. D4, Hepar sulf. D8, Hepar sulfuris, heparin sodium, humic acids, hydroxyethyl salicylate, Hypericum, ibuprofen, indomethacin, isobornyl acetate, potassium bichrome. D8, potassium sulf. D8, potassium-iron-phosphate-citrate complex, ketoprofen, Lachesis mutus D8, mountain pine oil, Levisticum, Rad. sicc. H 10%, levomenthol, *Mercurialis perennis* 2b Ø, *Mercurius bijodatus* D5, *Mercurius* solub. Hahnem, *Mercurius* solub. Hahnem. D8, methyl nicotinate, methyl salicylate (salicylic acid methyl ester), millefolium, myrtecaine, naloxone HCl, sodium thiosulfate, natural Eifelfango, nicoboxil, paracetamol, Pl. tota rec, quartz, rad. Harpagophyti (devil's claw), rad. *Harpagophytum procumbens, Resina laricis* (*Terebinthina laricina*), *Rhus toxicodendron* D6, Ruta D6 (rue), salicylic acid, sulfur, *Stibium metallicum praeparatum, Stibium sulfuratum nigrum* D1, Symphytum (comfrey), Symphytum D6, Symphytum offic. e rad. D6, Devil's Claw Root Extract, tilidine HCl $0.5H_2O$, tilidine phosphate, toxin from *Vipera ammodytes*, tramadol HCl, extract of nettle leaves, extract of horse chestnut seeds, extract of willow bark, extracts of aspen bark and leaves and/or triclosan.

Particularly preferably present in the preparation are panthenol (dexpanthenol), allantoin, bisabolol, urea, honey, e.g. manuka honey, hyaluronic acid, licochalcone, especially licochalcone A, polidocanol, propolis, zinc oxide, vitamins and/or provitamins such as vitamin A, C or E.

Derivatives and related and similar substances, also in combination or in combination with other substances, can also be present. Aloe vera, calendula, chamomile, witch hazel, St. John's wort, wheat germ, eucalyptus and extracts thereof or active ingredient combinations with these substances may also be present. Other possible active substances that promote wound healing are other herbal substances or mixtures of substances or plant extracts that promote wound healing. The use of one or a combination of the listed substances promote moist wound healing.

Very particular preference is given to panthenol, bisabolol, licochalcone A, polidocanol.

These substances can advantageously be used in the preparation in a proportion of 0.05 to 5% by weight, preferably in a proportion of 0.1 to 3% by weight, in particular 0.5 to 2.5% by weight, based on the total mass of the preparation.

Zinc oxide is also particularly preferred and can be used in the preparation in a proportion of 0.05 to 20% by weight, preferably in a proportion of 0.1 to 10% by weight, in particular 0.5 to 5% by weight, based on the total mass of the preparation.

Other possible active ingredients present in the preparation are local anesthetics that are suitable for surface anesthesia, such as e.g. Arsenicum album D12 (white arsenic), articaine, articaine HCl with epinephrine HCl, atropium sulf. D5, benzalkonium chloride, benzocaine, bupivacaine, bupiviacine HCl, chloroethane, cinchocaine, dibucaine, etidocaine, fomocaine, Formica rufa D12 (red forest ant), Hypericum perf. D5, lidocaine, lidocaine HCl, mepivacaine, mepivacaine HCl, methyl 4-hydroxybenzoate, oxybuprocaine, oxybuprocaine HCl, prilocaine, procaine, procaine HCl, procaine HCl with caffeine, propyl 4-hydroxybenzoate, quinisocaine, ropivacaine, ropivacaine HCl, sulfur D12, tetracaine, tetracaine HCl with macrogol lauryl ether and/or liquorice extracts.

Active ingredients for local pain relief such as benzocaine, procaine, lidocaine or prilocaine may be very particularly advantageously present in the preparation.

The use of local anesthetics offers an additional benefit of quick pain relief of an injured skin area. Local anesthetics can be used in the preparation in a proportion of 0.01 to 4% by weight, preferably in a proportion of 0.05 to 3% by weight, in particular 0.5 to 2.5% by weight, based on the total mass of the preparation.

Further particularly advantageous active ingredients for pain relief and anti-inflammation are cyclooxygenase inhibitors, such as acetylsalicylic acid or non-steroidal anti-inflammatory drugs (NSAIDs) such as diclofenac, ibuprofen, ketoprofen, benzydamine, benzyl nicotinate, bufexamac, etofenamate, flufenamic acid, heparinoids, naxoprophen, piroxicam, teniposide or indomethacin. Derivatives thereof and related and similar substances, also in combination or in combination with other substances, may be present in the preparation to provide additional pain relieving effect. Cyclooxygenase inhibitors can be present in a proportion of 0.01 to 10% by weight, preferably in a proportion of 0.1 to 5% and particularly preferably in a proportion of 0.2 to 2.5%. Herbal pain relievers such as aescin, guaiac wood, rhiz. Podophylli, Herba conii, Fol Hyoscyami, Fol Digitalis, *Echinacea purpurea*, ash bark, Delphinium staph, camphor, *Balsamum peruvianum*, comfrey root, goldenrod herb and Aethusa as well as extracts and combinations thereof can also be very advantageously present in the preparation, advantageously in a proportion of 0.1 to 5% by weight, particularly advantageously in a proportion of 0.5 to 3% by weight, based on the total mass of the preparation.

The preparation may also comprise antiseptic, antibiotic or antifungal active ingredients. An antiseptic effect prevents infections of the wound and thus offers an additional benefit to the formulation according to the invention.

Antiseptic, antibiotic and antifungal/antimycotic agents, which include, inter alia, aminoglycosides, prevent infections by preventing the growth of microorganisms. Antimicrobial metals that may be mentioned as advantageous are, for example, silver or salts thereof, chlorhexidine, octenidine hydrochloride, polyhexanide, povidone-iodine, taurolidine, 2,2'-methylenebis(6-bromo-4-chlorophenol), 2-biphenylol (instruments), 3,5-dibromo-4-hydroxybenzenesulfonic acid, 5-chloro-2-hydroxybenzoic acid, aluminum acetate tartrate, benzalkonium chloride, benzyl alcohol, biphenyl-2-ol, chlorofen, butane-1,3-diol, quinolin-8-ol sulfate, quinolinol sulfate potassium sulfate, chlorhexidine bis(D-gluconate), chlorhexidine digluconate, coco propylenediamine, didecyldimethylammonium chloride, ethacridine lactate $1H_2O$, glucoprotamine, glutaral, potassium thiocyanate, mecetronium ethyl sulfate, methyl 4-hydroxybenzoate, octenidine $2HCl$, phenoxyethanol, polihexanide, povidone-iodine, propyl 4-hydroxybenzoate, tosylchloramide sodium $3H_2O$, undecylenic acid, hydrogen peroxide, bifonazole, ammonium bituminosulfonate, bacitracin, benzoyl peroxide, quinolin-8-ol sulfate, chloramphenicol, chlortetracycline HCl, clindamycin, clindamycin 2-dihydrogenphosphate, clioquinol, erythromycin, framycetin sulfate (neomyicin B), fusidic acid $0.5H_2O$, gentamicin sulfate, purified turpentine oil, imiquimod, isotretinoin, larch turpentine, meclocycline (5-sulfo-2-hydroxybenzoate), metronidazole, miconazole nitrate, mupirocin, nadifloxacin, sodium bituminosulfonate (ICHTHYOL® sodium), sodium fusidate, neomycin sulfate, oxytetracycline HCl, podophyllotoxin, retapamulin, sulfadiazine silver, tetracycline HCl, tretinoin, dry extract from lemon balm leaves, tyrothricin. Particularly advantageously, chitosan, chlorhexidine, povidone-iodine, silver or silver sulfadiazine, triclosan, octenidine hydrochloride, polyhexanide, taurolidine or fungicides may be present.

Derivatives, similar substances and combinations thereof are thus also included according to the invention. Herbal antiseptic substances such as purified turpentine oil or larch turpentine may also be present in the preparation as active ingredients.

Particularly preferred in the case of antiseptic active ingredients are silver and salts thereof, octenidine and derivatives thereof, in particular octenidine dihydrochloride (octenidine and derivatives thereof also in combination with phenoxyethanol), iodine and derivatives thereof, povidone-iodine, polihexanide and derivatives thereof, in particular polihexanide hydrochloride, chlorhexidine and derivatives thereof, particularly the chloride and acetate, especially, in this case, chlorhexidine digluconate.

Antiseptic active ingredients may be present in the preparation in a proportion of 0.1 to 10% by weight, preferably in a proportion of 0.5 to 3% by weight, preferably in a proportion of 0.5 to 5% by weight, based on the total mass of the preparation. Other antiseptic agents, such as ethacridine lactate, may be present in a proportion of 0.05 to 1% by weight, advantageously in a proportion of 0.1 to 0.5% by weight.

Particularly preferred in the case of the antifungal active ingredients are a selection of ketoconazole, miconazole, ciclopirox (or its ethanolamine salt ciclopiroxolamine), amorolfine and derivatives thereof, naftifine, pyrrolnitrin, terbinafine, bifonazole and/or clotrimazole.

Antifungal active ingredients can be present in the preparation in a proportion of 0.1 to 10% by weight, preferably in a proportion of 0.5 to 3% by weight, preferably in a proportion of 0.5 to 5% by weight, based on the total mass of the preparation.

Active ingredients for faster healing of herpes blisters may particularly preferably be present in the preparation. Examples are heparin sodium, foscarnet sodium, tromantadine, idoxuridine, dimethyl sulfoxide, penciclovir and aciclovir. In addition to moist wound healing, a virustatic active ingredient offers an additional effect for faster healing of herpes blister outbreaks. Virustatics may advantageously be present in a proportion of 1 to 10% by weight, preferably in a proportion of 3 to 8% by weight. Herbal virustatics such as extracts of lemon balm leaves may be present in a proportion of 1 to 20% by weight, advantageously in a proportion of 5 to 15% by weight.

It is particularly preferred that cosmetic skin care active ingredients are present in the preparation.

The following active ingredients may advantageously be present, selected from the group of compounds comprising glycerin, panthenol, bisabolol, glycyrrhetic acid, urea, arctiin, alpha-lipoic acid, folic acid, phytoene, D-biotin, coenzyme Q10, alpha-glucosylrutin, tocopheryl acetate, carnitine, carnosine, caffeine, natural and/or synthetic isoflavonoids, glyceryl glucose, creatine, creatinine, taurine, magnolia, R-alanine and/or licochalcone A.

The active ingredient(s) are advantageously present in a proportion of 0.001-10% by weight, preferably 0.01-5% by weight, particularly preferably 0.05-1% by weight, preferably 0.01-0.5% by weight, based on the total mass of the preparation.

In a particularly preferred embodiment in the context of the present invention, the preparations comprise so-called moisturizers. Substances or mixtures of substances are referred to as moisturizers which cosmetic preparations impart the property, after application or distribution on the skin surface, of reducing the moisture release of the stratum corneum (also called transepidermal water loss (TEWL)) and/or to positively influence the hydration of the stratum corneum.

Advantageous moisturizers in the context of the present invention are, for example, glycerin, lactic acid and/or lactates. Further preferred skin moisturizers are particularly sodium lactate, butylene glycol, propylene glycol, biosaccharide gum-1, *Glycine soja*, ethylhexyloxyglycerin, pyrrolidone carboxylic acid, urea, glyceryl glucoside.

The amount of moisturizers, one or more compounds, is advantageously selected in the range of 1 to 20% by weight, preferably 3 to 15% by weight, particularly preferably 5 to 12% by weight, based in each case on the total weight of the preparation.

In addition to the lipids preferably specified, ceresin, cera microcristallina and/or paraffinum liquidum, especially ceresin, the preparation according to the invention preferably comprises further lipids, such as waxes from the group of fats, in particular from the group of natural waxes. The preparation preferably comprises one or more lipids selected from the group comprising Shorea stenoptera seed butter, hydrogenated vegetable oil, hydrogenated coco-glycerides, Butyrospermum parkii butter, *Theobroma cacao* (cocoa) seed butter, mango butter, hydrogenated palm kernel glycerides, hydrogenated palm glycerides, sunflower seed wax, soybean glycerides, Butyrospermum parkii unsaponifiables, Cera alba, beeswax, sugar cane wax, Cera carnauba, candelilla wax, Japanese wax, hydrogenated rapeseed oil, shellac wax, hydrogenated lecithin, hydrogenated soybean oil, from the group of synthetic waxes, in particular
    synthetic beeswax, synthetic wax, polyethylene, paraffin wax, ozokerite
    from the group of fatty acids, in particular
    palmitic acid, stearic acid,
    from the group of esters of fatty acids, in particular
    cetearyl nonanoate, methyl palmitate, glyceryl tribehenate, glyceryl laurate, glyceryl stearate, cetyl palmitate; shea butter oleyl esters, PEG-8 beeswax.

The preparation according to the invention preferably comprises cera microcristallina.

Furthermore, the lipid phase likewise may also advantageously comprise non-polar oils, for example those which are selected from the group of branched and unbranched hydrocarbons, in particular mineral oil, petroleum jelly (petrolatum), paraffin oil, squalane and squalene, polyolefins, hydrogenated polyisobutenes and isohexadecane. Among the polyolefins, polydecenes are the preferred substances.

Preferably selected is natural oil, vegetable oil or mineral oil, in particular paraffinum liquidum.

The total proportion of lipids, in particular ceresin, cera microcristallina and paraffinum liquidum, is selected in a proportion of more than 50% by weight up to a proportion of 90% by weight, particularly in the range from 75 to 85% by weight, based on the total mass of the preparation. If ceresin is present, its proportion is advantageously selected in the range from 8 to 15% by weight, based on the total mass of the preparation.

The cosmetic or dermatological formulations according to the invention may further comprise cosmetic auxiliaries and active ingredients, as are usually used in such formulations, e.g. preservatives, preservation aids, bactericides, substances to prevent foaming, dyes and color pigments, thickeners, moistening and/or moisturizing substances, anti-aging substances or other usual constituents of a cosmetic or dermatological formulation such as polyols, polymers, provided that the addition does not impair the required properties in terms of stability, sensory feel, care effects, freedom from water and freedom from substances of animal origin.

The cosmetic compositions in the context of the present invention, depending on their structure, may be used, for example, as a wound healing ointment, skin protection cream, nutrient cream, day or night cream.

The preparation according to the invention is preferably to be used as a non-therapeutic skin ointment.

Use of the preparation as a wound healing ointment is also preferred, in particular as a non-therapeutic wound healing ointment.

DETAILED DESCRIPTION OF EXEMPLARY EMBODIMENT OF THE INVENTION

The following example elucidates the formulations according to the invention.

Unless otherwise stated, the figures refer to parts by weight based on the total mass of the preparation.

Stability, sensory and haptic tests were carried out with this preparation.

| INCI | Proportion % by weight |
| --- | --- |
| Panthenol | 3.1 |
| Ceresin | 10 |
| Cera microcristallina + paraffinum liquidum | 41 |
| Paraffinum liquidum | 32.9 |
| Glyceryl stearate SE | 1.5 |
| Glyceryl stearate | 1.5 |
| Glycerin (aqua <1%) | 10 |
| | 100 |

It only became apparent that the use of a mixture of the two emulsifiers glyceryl stearate and glyceryl stearate SE made this preparation stable and at the same time much more appealing in terms of sensory feel and galvanic treatment.

Regarding the stability, especially good results were shown when combining 1.5% by weight glyceryl stearate and 1.5% by weight glyceryl stearate SE and 15% by weight ceresin. No oiling out was observed. The combination of 1.5% by weight glyceryl stearate and 1.5% by weight glyceryl stearate SE and 10% by weight ceresin also exhibited no oiling out. However, the ointment was softer in consistency and therefore more pleasant to the touch and feel. Therefore, a preparation comprising ceresin in a proportion of 8 to 12% by weight, in particular 10% by weight, based on the total mass of the preparation, is particularly preferred.

What is claimed is:

1. A cosmetic or dermatological preparation, wherein the preparation comprises
   (a) from 0.8% to 3% by weight of glyceryl stearate,
   (b) from 0.8% to 3% by weight of glyceryl stearate SE,
   (c) one or more lipids selected from ceresin, cera microcristallina and paraffinum liquidum,
   (d) less than 1% by weight of water, and
   (e) less than 0.1% by weight of each of cholesterol and lanolin alcohol,
   proportions by weight being in each case based on a total mass of the preparation.

2. The preparation of claim 1, wherein the preparation comprises from 1.2% to 1.8% by weight of (a).

3. The preparation of claim 1, wherein the preparation comprises from 1.2% to 1.8% by weight of (b).

4. The preparation of claim 2, wherein the preparation comprises from 1.2% to 1.8% by weight of (b).

5. The preparation of claim 1, wherein the preparation comprises from 8% to 15% by weight of ceresin.

6. The preparation of claim 1, wherein the preparation comprises from 9% to 12% by weight of ceresin.

7. The preparation of claim 4, wherein the preparation comprises from 9% to 12% by weight of ceresin.

8. The preparation of claim 1, wherein the preparation has a dynamic viscosity of more than 10,000 mPa*s at 25° C. and a shear rate of 10 s$^{-1}$.

9. The preparation of claim 8, wherein the preparation has a dynamic viscosity of form 18,000 mPa*s to 25,000 mPa*s.

10. The preparation of claim 1, wherein the preparation further comprises one or more active ingredients which promote wound healing.

11. The preparation of claim 1, wherein the preparation further comprises panthenol.

12. The preparation of claim 1, wherein the preparation further comprises one or more moisturizers.

13. The preparation of claim 1, wherein the preparation further comprises glycerol.

14. The preparation of claim 1, wherein the preparation comprises a total of from more than 50% by weight to 90% by weight of lipids.

15. The preparation of claim 1, wherein the preparation comprises a total of from 75% by weight to 85% by weight of lipids.

16. The preparation of claim 1, wherein the preparation comprises less than 0.1% by weight of water.

17. The preparation of claim 1, wherein the preparation comprises ceresin, cera microcristallina and paraffinum liquidum.

18. The preparation of claim 1, wherein the preparation comprises 1.5% by weight of (a), 1.5% by weight of (b) and from 10% to 15% by weight of ceresin.

19. The preparation of claim 1, wherein the preparation comprises 10% by weight of ceresin.

20. The preparation of claim 1, wherein the preparation is present as an ointment.

* * * * *